(12) United States Patent
Takahashi et al.

(10) Patent No.: US 7,176,163 B1
(45) Date of Patent: Feb. 13, 2007

(54) PHARMACOLOGICAL EFFECT POTENTIATORS FOR PESTICIDES

(75) Inventors: Naoyo Takahashi, Sakado (JP); Toshio Yasumura, Sakado (JP); Yoshihisa Tomoda, Sakado (JP); Hideki Usami, Sakado (JP)

(73) Assignees: Meija Seika Kaisha, Ltd., Tokyo (JP); Zeon Corp., Tokyo (JP)

( * ) Notice: Subject to any disclaimer, the term of this patent is extended or adjusted under 35 U.S.C. 154(b) by 0 days.

(21) Appl. No.: 09/926,064

(22) PCT Filed: Feb. 24, 2000

(86) PCT No.: PCT/JP00/01073

§ 371 (c)(1),
(2), (4) Date: Aug. 23, 2001

(87) PCT Pub. No.: WO00/49872

PCT Pub. Date: Aug. 31, 2000

(51) Int. Cl.
*A01N 57/00* (2006.01)
*A01N 43/50* (2006.01)
*A01N 43/52* (2006.01)
*A61K 31/415* (2006.01)

(52) U.S. Cl. .................. 504/128; 504/139; 514/119; 514/395

(58) Field of Classification Search .................. 514/573, 514/119, 395; 504/128, 139
See application file for complete search history.

(56) References Cited

U.S. PATENT DOCUMENTS 5,776,860 A    7/1998  Kamuro et al. ............. 504/313

FOREIGN PATENT DOCUMENTS

| EP | 0888715 | * | 1/1999 |
| JP | 08059408 | | 3/1996 |
| JP | 08113503 | | 5/1996 |
| JP | 0 888 715 A1 | | 1/1999 |
| JP | 2000016902 | | 1/2000 |
| JP | 1 031 554 A1 | | 8/2000 |

* cited by examiner

*Primary Examiner*—Alton N. Pryor
(74) *Attorney, Agent, or Firm*—Armstrong, Kratz, Quintos, Hanson & Brooks, LLP

(57) ABSTRACT

By applying a compound selected from jasmonic acid represented by the following general formula (I) or 2-substituted form of jasmonic acid or derivatives thereof or salts thereof, the pharmacological action of a pesticide such as a microbicide or a herbicide applied to the plant is enhanced.

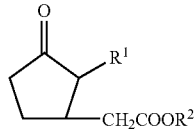

(I)

(wherein $R^1$ is an alkyl group or an alkenyl group, and $R^2$ is a hydrogen atom, an alkyl group, an alkenyl group, an alkynyl group or a hydroxyalkyl group).

11 Claims, No Drawings

PHARMACOLOGICAL EFFECT POTENTIATORS FOR PESTICIDES

TECHNICAL FIELD

The present invention relates to jasmonic acid or its derivatives or salts and to a pharmacological action enhancer for pesticides using the same.

BACKGROUND ART

Under the circumstances where promotion of environment protecting type or environment harmonizing type agriculture is being increasingly demanded, chemical high farming on which agricultural production to date has been centered is thought again and it has now become the race to develop an efficient method for using chemical fertilizers, chemical pesticides and so forth. To cope with this problem, approaches have been made on the side of use of organic fertilizers and improvement in the formulation of fertilizers and pesticides. For example, there is a method of controlling the elution rate of active ingredient to allow it to be eluted at the desired time or sustain its pharmacological action. Besides it, in the case of pesticides, for example, a method that uses a spreader to improve the adhesive property of the pesticide on the surface of a plant has been conventionally adopted. However, in these methods it is not always the case that the minimum necessary application amounts are used but in actuality, they are in a large excess over the necessary amounts. Particularly, in protected plant husbandry such as growing in greenhouse where works under closed environment are performed in the main, a more efficient method for applying chemicals are being demanded so that no adverse influence is given on the workers.

Jasmonic acid was found out as a new plant hormone and has been applied to agriculture as a plant growth enhancer (WO96/06529) or as a low temperature injury resistor (JP-A-08-113503). Furthermore, a method for producing various jasmonic acid based compounds has been developed (JP-A-11-140022) and an abscission layer formation enhancer containing jasmonic acid or its analog itself as an active ingredient together with an ethylene action substance has been disclosed (JP-A-2000-16902).

However, there has been no knowledge on the enhancement of the pharmacological actions of other pesticides by jasmonic acid or its derivatives.

DISCLOSURE OF THE INVENTION

Under the circumstances, the present inventors have made extensive studies with a view to screening compounds that enhance the uptake of pesticides by the plant body. As a result they have found out that specified jasmonic acid or derivatives thereof have an action of enhancing absorption of pesticides and increasing the pharmacological action thereof. The present invention has been accomplished based on the findings.

According to the present invention, there is provided a pharmacological action enhancer for pesticides comprising one or more compounds selected from the compounds represented by the following general formula (I) and salts thereof as an active ingredient

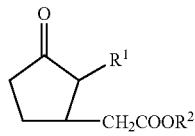

(wherein $R^1$ is an alkyl group or an alkenyl group, and $R^2$ is a hydrogen atom, an alkyl group, an alkenyl group, an alkynyl group or a hydroxyalkyl group).

The present invention also provides the above-mentioned pharmacological action enhancer in which $R^1$ is selected from a pentyl group and a pentenyl group, and $R^2$ is selected from a hydrogen atom, a methyl group, an ethyl group, a propyl group, a pentyl group, an allyl group, a butenyl group, a pentenyl group or a butynyl group.

The above-mentioned pesticide includes microbicides and herbicides.

The present invention further provides the above-mentioned pharmacological action enhancer that comprises a solid carrier, a liquid carrier or a controlled release carrier.

Also, the present invention provides the above-mentioned pharmacological action enhancer that is used by spraying, dipping, watering, hydroponic culture, medium mixing, fumigation, or natural diffusion.

Furthermore, the present invention provides a method for enhancing the pharmacological action of pesticides comprising the step of applying the above-mentioned pharmacological action enhancer and pesticides to a plant.

Hereinafter, the present invention will be described in detail.

The compounds used in the present invention are represented by the general formula (I) described above. Note that jasmonic acid (3-oxo-2-(2-pentenyl)-,[1R-[1α,2β-(z)]]-cyclopentylacetic acid) is a compound of the general formula (I) in which $R^1$ is a 2-pentenyl group and $R^2$ is a hydrogen atom.

In the present specification, the term "alkyl group" means a linear, branched, or cyclic alkyl group having 1 to 20 carbon atoms, preferably 1 to 8 carbon atoms, and more preferably 1 to 6 carbon atoms. The term "alkenyl group" means a linear or branched alkenyl group having 2 to 20 carbon atoms, preferably 2 to 8 carbon atoms, and more preferably 2 to 6 carbon atoms. The term "alkynyl group" means a linear or branched alkynyl group having 2 to 20 carbon atoms, preferably 2 to 8 carbon atoms and more preferably 3 to 6 carbon atoms. The term "hydroxyalkyl group" means a linear or branched hydroxyalkyl group having 1 to 20 carbon atoms, preferably 1 to 8 carbon atoms, and more preferably 1 to 3 carbon atoms.

Specific examples of $R^1$ may include, for example, a methyl group, an ethyl group, an n-propyl group, an isopropyl group, an n-butyl group, a sec-butyl group, a t-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, an n-heptyl group, an isoheptyl group, an n-octyl group, an isooctyl group, a 2-ethylhexyl group, a nonyl group, a vinyl group, an allyl group, a 2-butenyl group, a 3-butenyl group, an isobutenyl group, a 4-pentenyl group, a 3-pentenyl group, a trans-2-pentenyl group, a cis-2-pentenyl group, a 1-pentenyl group, a 3-methyl-2-pentenyl group, a 5-hexenyl group, a 3-hexenyl group, a 2-hexenyl group, a heptenyl group, an octenyl group, a nonenyl group, and a decenyl group. Among these, an ethyl group, an n-propyl group, an isopropyl group, an n-butyl group, a sec-butyl group, a t-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, an allyl group, a 2-butenyl group, a 3-butenyl group, an isobutenyl group, a 4-pentenyl group, a 3-pentenyl group, a trans-2-pentenyl group, a cis-2-pentenyl group, a 1-pentenyl group, a 3-methyl-2-pentenyl, a 5-hexenyl group, a 3-hexenyl group, a 2-hexenyl group and so forth are preferred, with an n-pentyl group, an isopentyl group, a 2-methylbutyl group, a 1-methylbutyl group, a 4-pentenyl group, a 3-pentenyl group, a trans-2-pentenyl group, a cis-2-pentenyl group, a 1-pentenyl group and so forth being particularly preferred.

Specific examples of $R^2$ described above may include hydrogen, a methyl group, an ethyl group, a propyl group, a butyl group, a pentyl group, a hexyl group, a 2-methylbutyl group, a vinyl group, an allyl group, a 3-butenyl group, a 2-pentenyl group, a 4-methyl-3-pentenyl group, a 2-hexenyl group, a propargyl group, a 3-butynyl group, a 2-pentynyl group, a 3-hexynyl group, a hydroxymethyl group, a hydroxyethyl group, a hydroxypropyl group and so forth.

The compounds represented by the general formula (I) described above include jasmonic acid and 2-substituted form of jasmonic acid and their esters. Hereinafter, the compound represented by the general formula (I) described above is sometimes referred to as a jasmonic acid based compound and the ester thereof is sometimes referred to as a jasmonic acid based compound ester.

Specific examples of the jasmonic acid based compound ester may include, for example, methyl (2-pentyl-3-oxocyclopentyl)acetate, methyl [2-(2-pentenyl)-3-oxocyclopentyl]acetate, methyl [2-(3-pentenyl)-3-oxocyclopentyl]acetate, ethyl (2-pentyl-3-oxocyclopentyl)acetate, ethyl [2-(2-pentenyl)-3-oxocyclopentyl]acetate, propyl (2-pentyl-3-oxocyclopentyl)acetate, propyl [2-(2-pentenyl)-3-oxocyclopentyl]acetate, propyl [2-(3-pentenyl)-3-oxocyclopentyl]acetate, propyl [2-(2-methylbutyl)-3-oxocyclopentyl]acetate, propyl [2-(2,2-dimethylpropyl)-3-oxocyclopentyl]acetate, isopropyl (2-pentyl-3-oxocyclopentyl)acetate, isopropyl [2-(2-pentenyl)-3-oxocyclopentyl]acetate, isopropyl [2-(3-pentenyl)-3-oxocyclopentyl]acetate, butyl (2-pentyl-3-oxocyclopentyl)acetate, butyl [2-(2-pentenyl)-3-oxocyclopentyl]acetate, butyl [2-(3-pentenyl)-3-oxocyclopentyl]acetate, isobutyl (2-pentyl-3-oxocyclopentyl)acetate, isobutyl [2-(2-pentenyl)-3-oxocyclopentyl]acetate, sec-butyl (2-pentyl-3-oxocyclopentyl)acetate, sec-butyl [2-(2-pentenyl)-3-oxocyclopentyl]acetate, t-butyl (2-pentyl-3-oxocyclopentyl)acetate, pentyl (2-pentyl-3-oxocyclopentyl)acetate, pentyl [2-(2-pentenyl)-3-oxocyclopentyl]acetate, 2-methylbutyl (2-pentyl-3-oxocyclopentyl)acetate, hexyl (2-pentyl-3-oxocyclopentyl)acetate, hexyl [2-(2-pentenyl)-3-oxocyclopentyl]acetate, heptyl [2-(2-pentenyl)-3-oxocyclopentyl]acetate, octyl (2-pentyl-3-oxocyclopentyl)acetate, octyl [2-(2-pentenyl)-3-oxocyclopentyl]acetate, decyl (2-pentyl-3-oxocyclopentyl)acetate, allyl (2-pentyl-3-oxocyclopentyl)acetate, cis-2-pentenyl (2-pentyl-3-oxocyclopentyl)acetate, trans-2-hexenyl (2-pentyl-3-oxocyclopentyl)acetate, butenyl (2-pentyl-3-oxocyclopentyl)acetate, 2-pentenyl (2-pentyl-3-oxocyclopentyl)acetate, 4-methyl-3-pentenyl (2-pentyl-3-oxocyclopentyl)acetate, cis-3-hexenyl (2-pentyl-3-oxocyclopentyl)acetate, propargyl (2-pentyl-3-oxocyclopentyl)acetate, 2-pentynyl (2-pentyl-3-oxocyclopentyl)acetate, 3-butynyl (2-pentyl-3-oxocyclopentyl)acetate, 3-hexynyl (2-pentyl-3-oxocyclopentyl)acetate, 2-hydroxyethyl (2-pentyl-3-oxocyclopentyl)acetate, 2-hydroxypropyl (2-pentyl-3-oxocyclopentyl)acetate, allyl [2-(2-pentenyl)-3-oxocyclopentyl]acetate, propargyl [2-(2-pentenyl)-3-oxocyclopentyl]acetate, 3-butenyl [2-(2-pentenyl)-3-oxocyclopentyl]acetate, 2-pentenyl [2-(2-pentenyl)-3-oxocyclopentyl]acetate, 3-butynyl [2-(2-pentenyl)-3-oxocyclopentyl]acetate, cis-3-hexenyl [2-(2-pentenyl)-3-oxocyclopentyl]acetate and so forth.

The jasmonic acid based compound esters described above can be produced by a common method. For example, the jasmonic ester corresponding to the general formula (I) in which $R^1$ is a pentyl group and $R^2$ is an alkyl group can be readily obtained by subjecting 2-pentylcyclopenten-1-one and a malonic acid alkyl ester to Michael addition followed by decarbonation (cf. Japanese Patent Application Laid-open No. Hei 11-140022, and Japanese Patent Application Laid-open No. 2000-16902). Jasmonic acid can be readily obtained, for example, by hydrolyzing a jasmonic acid ester with a base or acid (cf. JP-A-11-140022,and JP-A-2000-16902).

Note that stereo isomers based on one or more asymmetric carbon atoms or optional mixtures thereof, racemi forms, and geometric isomers based on one or more olefinic double bonds or optional mixtures thereof of the compound represented by the general formula (I) are all included in the scope of the present invention.

Preferred salts in the present invention may include alkali metal salts or alkaline earth metal salts, such as sodium salts, potassium salts or calcium salts, organic alkali salts such as pyridine salts and triethylamine salts.

Preferred compounds for natural diffusion application utilizing volatility include the compounds of the general formula (I) in which $R^1$ is a pentyl group or a pentenyl group and $R^2$ is a hydrogen atom or a methyl group. When they are used for spraying, the compounds of the general formula (I) in which $R^1$ is a pentyl group or a pentenyl group and $R^2$ is an n-propyl group are preferred.

The compounds of the general formula (I) and their salts used in the present invention may be used singly or any two or more of them may be used in combination. In the present invention, the target pesticides include microbicides and herbicides but are not particularly limited as far as the actions thereof can be enhanced by the compounds of the general formula (I) and salts thereof.

In the present invention, that the action of a pesticide is enhanced means that application of the pesticide in combination of the pharmacological action enhancer of the present invention to a plant exhibits a pharmacological action higher than that given by application of the pesticide alone to the plant. The mechanism of pharmacological action enhancement in the present invention is presumed to be attributable to enhancement of absorption of the pesticide to the plant body by the compound of the general formula (I) or its salts. However, in the present invention, as far as the pharmacological action of pesticide is enhanced, it does not matter whether the enhancement is due to the enhancement of absorption of the pesticide or an increase in the specific activity of the pesticide itself due to a synergistic effect.

In the present invention, the microbicides include, for example, copper microbicides, inorganic microbicides, organosulfur microbicides, organochlorine based microbicides, organophosphorus microbicides, melanine biosynthesis inhibitors, benzoimidazole based microbicides, dicarboximide based microbicides, acid amide based microbicides, sterol biosynthesis inhibitors, methoxyacrylate based microbicides, anilinopyrimidine based microbicides, synthetic antibacterial agents, soil sterilizers, other synthetic sterilizers that are not classified into the above, antibiotics microbicides and so forth.

The herbicides include, for example, phenoxy acid based herbicides, diphenyl ether based herbicides, carbamate based herbicides, acid amide based herbicides, urea based herbicides, sulfonyl urea based herbicides, pyrimidyloxybenzoic acid based herbicides, triazine based herbicides, diazine based herbicides, diazole based herbicides, bipyridium based herbicides, dinitroaniline based herbicides, aromatic carboxylic acid based herbicides, fatty acid based herbicides, organophosphorus based herbicides, amino acid based herbicides, other organic herbicides that are not classified into the above, inorganic herbicides and so forth.

In the present invention, the term pharmacological action of a pesticide means microbicidal action in the case of microbicides, or herbicidal action in the case of herbicides.

In the present invention, the plant that is the target of application is not particularly limited and includes, for example, cereals such as rice plant and wheat, fruit vegetables such as cucumber and tomato, foliage vegetables such as cabbage and spinach, fruit trees such as persimmon and peach, flower plants such as margarette, arbores such as camellia and Japanese cypress, beans such as soybean, grasses such as Korean lawn grass and bent grass, tubers such as potato and sweet potato, alliums such as leek and onion, and pastures such as alfalfa and clover.

The test examples hereinbelow show that the compounds represented by the general formula (I) enhance the actions of Benomyl (methyl 1-(butylcarbamoyl)-2-benzimidazolecarbamate), microbicide, and Bialafos (L-2-amino-4-[(hydroxy)(methyl)phosfinoyl]butyryl-L-alanyl-alanine), herbicide. However, the chemical to which the present invention can be applied is not limited thereto.

The compounds represented by the general formula (I) and salts thereof can increase the action of a pesticide by applying them as mixtures with the pesticide or by applying them alone in advance prior to applying the pesticide or at the same time with the application of the pesticide.

The pharmacological action enhancer for pesticides according to the present invention can be applied by spraying, dipping, watering, hyrdoponic culture, medium mixing, fumigation, or natural diffusion. It can be optionally formulated into preparations together with a carrier such as a solid carrier, a liquid carrier or a controlled release carrier depending on the intended application method. The formulation includes aqueous solution, emulsion, organic solvent solution, wettable powder, tablet, powder, flowable preparation, aerosol, and so forth.

In the case where the compounds represented by the general formula (I) and salts thereof are to be sprayed, they may be diluted to appropriate concentrations by using a liquid carrier such as water or an organic solvent such as an alcohol or a solid carrier such as clay or sugar in combination with other auxiliaries such as a spreader as needed before they can be used. In the case where they are mixed with a pesticide, they may be directly mixed with the pesticide and applied according to the intended use method.

In the case of dipping, watering, hydroponic culture, medium mixing or the like, they may be diluted to appropriate concentrations by using a liquid carrier such as water or an organic solvent such as an alcohol in combination with other auxiliaries such as a spreader as needed before they can be used. Alternatively, they may also be mixed with a fertilizer or a medium.

In the case of natural diffusion, in addition to a method of directly evaporating a volatile compound, a method of natural diffusion by standing a preparation made of a solid carrier such as filter paper, activated carbon or bead or a controlled release carrier such as gel and the compound of the general formula (I) or salt thereof mixed with and adsorbed by the carrier is preferred. In the case where the compound of the general formula (I) or salt thereof is to be mixed with gel, an oil gel employed in air fresheners may be used. The compounds or mixture and adsorbate may be used after placing them in a container having a lid that can be opened or closed freely. This facilitates not only handling of the substance but also control of the evaporation amount by opening or closing of the lid of the container. In the case of fumigation, the evaporation is effected by warming.

The concentration of the compound represented by the general formula (I) or salt thereof is not particularly specified depending on the type of target plant, use method, use time, use mode and so forth. In the case where it is applied as an aqueous solution by using a liquid carrier, the concentration is preferably from 0.001 to 5.0 ppm and more preferably from 0.01 to 1.0 ppm. In the case of fumigation treatment or natural diffusion, a concentration of from 5 to 50 $\mu l/m^3$ is preferred.

BEST MODE FOR CARRYING OUT OF THE INVENTION

Hereinafter, the present invention will be described in detail by preparation examples and test examples. However, the present invention is not limited these examples.

Preparation Example 1

Preparation of Methyl Jasmonate Containing Oil Gel

A pharmacological action enhancing gel was made using dibenzylidenesorbitol gel (purchased from E. C. Chemical Co., Ltd. (2-28-3, Kasuga Nishimachi, Hirakata-shi, Osaka-fu), cf. Japanese Patent Application Laid-open No. Sho 59-77859) as methyl jasmonate (methyl (2-pentenyl-3-oxocyclopentyl)acetate) containing oil gel and mixing the methyl jasmonate upon preparation. 3-Methyl-3-methoxybutanol was purchased from Kanto Chemical Co., Ltd. (manufacturer: ACROS ORGANICS, N.J., USA: 1-800-ACROS-01).

| | |
|---|---|
| (1) Dibenzylidenesorbitol | 5 parts by weight |
| (2) 3-Methyl-3-methoxybutanol | 94 parts by weight |
| (3) Methyl jasmonate | 1 part by weight |

(1) and (2) above were mixed and the mixture was slowly stirred at 80° C. under reflux until it was dissolved. Then the temperature of the solution was decreased to 60° C. and (3) above was mixed, followed by cooling to prepare methyl jasmonate containing oil gel. Upon use, the product was placed in a container with a lid and the evaporation amount was controlled by opening or closing the lid or the like.

Test Example 1

Tests on Microbicide Absorption Enhancement by Spraying Jasmonic Acids

In the present test, Benlate (registered trademark, manufactured by DuPont Corp., containing 50% of Benomyl as the main component) was used as microbicide. As a test material, cotyledon of cucumber (variety: Yotsuba) was used and absorption amount of the microbicide (hereinafter, referred to as "Benomyl absorption amount") was measured. To the cucumber on day 10 after the seeding was uniformly sprayed 0.22 ml per individual of 0.1% Benlate solution (0.05% Benomyl containing solution) that contains methyl jasmonate (hereinafeter, abbreviated as "MeJA") or n-propyl (2-pentyl-3-oxocyclopentyl)acetate, also named n-propyldihydrojasmonic acid (hereinafter, abbreviated as "PDJ") and the cucumber was placed in a glass-made chamber. MeJA or PDJ was mixed to make 0.001 ppm, 0.01 ppm, 0.1 ppm, 1.0 ppm, or 5.0 ppm based on the Benlate solution amount and applied simultaneously. After sealing the lid of the chamber, the cucumber was cultivated in an air-conditioned room. As a control, similarly Benlate-treated cucumber seedlings were placed in a separate chamber and cultivated.

After two days of cultivation, the cotyledons were cut off and the surfaces of them were washed carefully with a neutral detergent. The cotyledons were ground and extracted with heating. The treatment of extraction solution and quantitation of Benomyl were carried out by high performance liquid chromatography referring to the quantitation method of Benomyl in Residual Pesticide Standards Handbook (Kagaku Kogyo Nippo, 1995, pp843–845) using 2-methylbenzimidazolecarbamate, which is a metabolite of Benomyl, as an indicator. Table 1 shows the results in relative values of Benomyl absorption amount in each lot to that of control lot. As will be apparent from Table 1, enhancement of the absorption of Benomyl by application of MeJA or PDJ was observed.

TABLE 1

| Treated lot | Relative value (%) of Benomyl absorption amount to that of control lot |
| --- | --- |
| Control lot | 100 |
| MeJA 0.001 ppm | 96 |
| MeJA 0.01 ppm | 124 |
| MeJA 0.1 ppm | 127 |
| MeJA 1.0 ppm | 142 |
| MeJA 5.0 ppm | 113 |
| PDJ 0.001 ppm | 103 |
| PDJ 0.01 ppm | 136 |
| PDJ 0.1 ppm | 118 |
| PDJ 1.0 ppm | 110 |

Test Example 2

Tests on Benomyl Absorption Enhancement by Fumigation of Methyl Jasmonate

MeJA was applied as follows. MeJA Stock solution was charged in an open Petri dish ($\phi$60 mm) to 25 $\mu$l/m$^3$, which was placed in a glass-made chamber and then sealed and allowed to naturally diffuse. Then, cucumber seedlings uniformly sprayed with 0.22 ml per individual of 0.1% Benlate solution (0.05% Benomyl containing solution) were placed and sealed. This was cultivated in an air-conditioned room. As a control cucumber seedlings that had been similarly treated with Benlate but not fumigated with MeJA were placed in a separate chamber and cultivated. Extraction was made in the same manner as in Test Example 1 and comparative quantitation in comparison with control lot was made. As a result, an increase in Benomyl absorption amount by MeJA fumigation was observed as shown in Table 2.

TABLE 2

| Treated lot | Relative value (%) of Benomyl absorption amount to that of control lot |
| --- | --- |
| Control lot | 100 |
| MeJA Fumigation | 144 |

Test Example 3

Tests on Powdery Mildew Preventive Effect Improvement by PDJ Spraying

Cucumber seedlings were cultivated in the same manner as in Test Example 1 and uniformly sprayed with 0.22 ml per individual of 0.1% Benlate solution (0.05% Benomyl containing solution) mixed with PDJ in an amount of 0.01 ppm or 0.1 ppm based on the amount of Benlate solution. After 3 days from the application of Benlate solution, a spore suspension of cucumber powdery mildew (*Sphaeheca fuliginea*) prepared to 1.0×10$^5$ cells/ml was sprayed (0.2 ml per individual) on a first true leaf of each seedling and the seedlings were cultivated in a glass-made chamber. After 10 days, powdery mildew plagues were counted. Table 3 shows the results as a morbidity defined as a ratio of plaque number in each treated lot to that of control lot, as represented by the following equation.

Morbidity=(Average of powdery mildew plaque number on cucumber first true leaf in each treated lot)/(Average of powdery mildew plaque number on cucumber first true leaf in control lot)×100

Here, the control lot means a lot that is treated with a Benlate solution containing no PDJ. Thus, it was confirmed that PDJ spraying further increased the powdery mildew preventive effect of Benomyl.

TABLE 3

| Treated lot | Powdery Mildew Morbidity |
| --- | --- |
| Control lot | 100 |
| PDJ 0.01 ppm | 70 |
| PDJ 0.1 ppm | 88 |

Test Example 4

Tests on Powdery Mildew Preventive Effect Improvement by Methyl Jasmonate Fumigation Cucumber seedlings were cultivated in the same manner as in Test Example 2 and uniformly sprayed with 0.22 ml per individual of 0.1% Benlate solution (0.05% Benomyl containing solution). Thereafter, MeJA fumigation was performed as follows. MeJA Stock solution was charged in an open Petri dish ($\phi$60 mm) to 25 $\mu$l/m$^3$, which was placed in a glass-made chamber and then sealed. On day 3 after the initiation of the fumigation, cucumber powdery mildew was infected in the same manner as in Test Example 3 and powdery mildew plaque number was counted. Table 4 shows the plaque number in the fumigated lot to that of control lot as morbidity. The control lot means a lot in which no MeJA fumigation was performed. Thus, it was confirmed that MeJA fumigation further improved the powdery mildew preventive effect of Benomyl.

TABLE 4

| Treated lot | Powdery Mildew Morbidity |
|---|---|
| Control lot | 100 |
| MeJA Fumigation | 76 |

Test Example 5

Tests on Herbicidal Effect Enhancement by PDJ Spraying

Seeds of *Poa annua* were sown on commercially available cultivation soil for raising seedlings and after about 2 weeks of cultivation, seedlings of about 6 cm in height were obtained. For each lots, tests were performed in 5 series each with 3 individuals. The herbicide used was Herbie liquid (registered trademark of Meiji Seika Kaisha Limited, 18% Bialaphos containing solution) diluted to 1/1000. PDJ was used as a pharmacological action enhancer and this was added in an amount of 0.01 ppm based on the liquid amount of the herbicide. Application to the plant body was performed by spraying in an amount of 5 ml/15 individuals. After 2 weeks from the application, the dry weight of above-ground part was measured and mortality was calculated in accordance with the following equation and the effect was compared. As a result, as shown in Table 5, it was confirmed hat the addition of PDJ increased wilting mortality to enhance the herbicidal action.

Wilting Mortality={1−(growth amount of applied lot/growth amount of non-applied lot)}×100

TABLE 5

| Herbie liquid (Dilution) | PDJ (ppm) | Wilting Mortality |
|---|---|---|
| 1/1000 | 0 | 67.7 |
| 1/1000 | 0.01 | 81.2 |

Test Example 6

Tests on Microbicide Absorption Enhancement by Various Jasmonic Acid Derivatives Tests on microbicide absorption enhancement were performed in the same manner as in Test Example 1 using the following compounds. Common names and abbreviations of each compound are shown in the brackets. The compounds were synthesized in the same manner as in the examples in Japanese Patent Application Laid-open No. Hei 11-140022.

1. 2-pentyl-3-oxocyclopentyl acetate (dihydrojasmonic acid: DJA)
2. allyl (2-pentyl-3-oxocyclopentyl)acetate (allyl dihydrojasmonate: ADJ)
3. 2-pentenyl (2-pentyl-3-oxocyclopentyl)acetate (dihydrojasmonic acid-2-pentenyl: PEDJ)
4. 3-butenyl (2-pentyl-3-oxocyclopentyl)acetate (dihydrojasmonic acid-3-butenyl: BEDJ)
5. 3-butynyl (2-pentyl-3-oxocyclopentyl)acetate (butynyl dihydrojasmonate : BYDJ)

Each compound was mixed so that it occupies 0.01 ppm based on the Benlate solution and given at the same time. Extraction and quantitation were practiced by the methods described in Test Example 1. The results are shown as relative values of Benomyl absorption amount in each lot to that of control. As a result, as will be apparent from Table 6, enhancement of absorption of Benomyl was confirmed.

TABLE 6

| Treated lot | Relative value (%) of Benomyl absorption amount to that of control lot |
|---|---|
| Control lot | 100 |
| DJA | 130 |
| ADJ | 145 |
| PEDJ | 130 |
| BEDJ | 155 |
| BYDJ | 130 |

Industrial Applicability

In the present invention, application of jasmonic acid or its derivatives, or salts thereof enables enhancement of absorption of pesticides by plants and enhancement of their pharmacological actions.

What is claimed is:

1. A pharmacological action enhancer composition, comprising:
   benomyl or bialaphos; and
   one or more compounds selected from the compounds represented by the following general formula (I) and salts thereof as an active ingredient

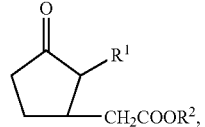

(wherein $R^1$ is an alkyl group or an alkenyl group, and $R^2$ is a hydrogen atom, an alkyl group, an alkenyl group, an alkynyl group or a hydroxyalkyl group).

2. The pharmacological action enhancer composition according to claim 1, wherein $R^1$ is selected from a pentyl group and a penetenyl group, and $R^2$ is selected from a hydrogen atom, a methyl group, an ethyl group, a propel group, a pentyl group, an allyl group, a butenyl group, a pentenyl group or a butynyl group.

3. The pharmacological action enhancer composition according to claims 1 to 2, further comprising a solid carrier, a liquid carrier or a controlled release carrier.

4. A method for enhancing the pharmacological action of benomyl or bialaphos, comprising the step of applying a pharmacological action enhancer and benomyl or bialaphos to a plant,
   wherein said pharmacological action enhancer is one or more compounds selected from the compounds represented by the following general formula (I) and salts thereof as an active ingredient

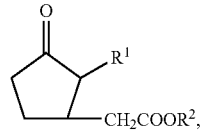

(wherein $R^1$ is an alkyl group, or alkenyl group, and $R^2$ is a hydrogen atom, an alkyl group, an alkenyl group, an alkynyl or a hydroxyalkyl group).

5. The method for enhancing the pharmacological action of benomyl or bialaphos according to claim 4, wherein the pharmacological action enhancer is applied to a plant at the same time with the benomyl or bialaphos or before applying the benomyl or bialaphos.

6. The method of claim 4, wherein said step of applying is performed by spraying, dipping, watering, hydrophonic culture, medium mixing, fumigation, or natural diffusion.

7. A method for enhancing the pharmacological action of benomyl or bialaphos, comprising the step of applying a pharmacological action enhancer to a plant and the step of applying benomyl or bialaphos to the plant, wherein said pharmacological action enhancer is one or more compounds from the compounds represented by the following general formula (I) and salts thereof as an active ingredient

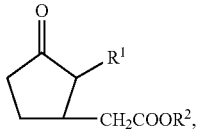
(I)

(wherein $R^1$ is an alkyl group or alkenyl group, and $R^2$ is a hydrogen atom, an alkyl group, an alkenyl group, an alkynyl or a hydroxyalkyl group).

8. A method for enhancing the pharmacological action of benomyl or bialaphos, comprising the step of applying benomyl or bialaphos to a plant and the step of applying a pharmacological action enhancer to the plant, wherein said pharmacological action enhancer is one or more compounds from the compounds represented by the following general formula (I) and salts thereof as an active ingredient

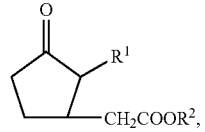
(I)

(wherein $R^1$ is an alkyl group or alkenyl group, and $R^2$ is a hydrogen atom, an alkyl group, an alkenyl group, an alkynyl or a hydroxyalkyl group).

9. The method according to any one of claims 4, 7 and 8, wherein the applying pharmacological action enhancer to the plant is performed by fumigation or natural diffusion.

10. The method according to any one of claims 4, 7 and 8, wherein the enhancement of the pharmacological action of benomyl or bialaphos is caused by an increased intake of benomyl or bialaphos by the plant by means of the pharmacological action enhancer.

11. The method according to any one of claims 4, 7 and 8, wherein said pharmacological action enhancer is methyl jasmonate or n-propyl dihydrojasmonic acid.

* * * * *

UNITED STATES PATENT AND TRADEMARK OFFICE
CERTIFICATE OF CORRECTION

PATENT NO.        : 7,176,163 B1
APPLICATION NO.   : 09/926064
DATED             : February 13, 2007
INVENTOR(S)       : Takahashi et al.

It is certified that error appears in the above-identified patent and that said Letters Patent is hereby corrected as shown below:

On the title page:
in item (73) the assignee, change "Meija Seika Kaisha, Ltd.," to be --Meiji Seika Kaisha, Ltd.--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,176,163 B1 |
| APPLICATION NO. | : 09/926064 |
| DATED | : February 13, 2007 |
| INVENTOR(S) | : Takahashi et al. |

Page 1 of 1

It is certified that error appears in the above-identified patent and that said Letters Patent is hereby corrected as shown below:

<u>On the Title Page:</u>
please insert item
--(30)        Foreign Application Priority Data
         Feb. 26, 1999   (JP)    .........   11-51395--

<u>In column 10:</u>
in claim 1 on line 37 change "(wherein ......" to be --wherein ......--
         on line 39 change "......group)." to be --......group.-- in claim 3 on line 47 change "according to claims 1 to 2," to be --according to any one of claims 1 to 2,-- in claim 4 on line 65 change "(wherein ......" to be --wherein ......--
         on line 68 change "..... group)." to be --......group.--

<u>In column 11:</u>
in claim 7 on line 13 change "more compounds from" to be --more compounds selected from--
         on line 24 change "(wherein ......" to be --wherein ......--
         on line 26 change "...... group)." to be --..... group.--

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,176,163 B1
APPLICATION NO. : 09/926064
DATED : February 13, 2007
INVENTOR(S) : Takahashi et al.

It is certified that error appears in the above-identified patent and that said Letters Patent is hereby corrected as shown below:

In column 12:
in claim 8 on line 2 change "more compounds from" to be -- more compounds selected from --
on line 14 change "(wherein .....)" to be -- wherein ....... --
on line 16 change "...... group)." to be -- ..... group. --

Signed and Sealed this

Third Day of February, 2009

JOHN DOLL
*Acting Director of the United States Patent and Trademark Office*